(12) United States Patent
Miller

(10) Patent No.: US 8,870,872 B2
(45) Date of Patent: Oct. 28, 2014

(54) IMPACT-DRIVEN INTRAOSSEOUS NEEDLE

(75) Inventor: Larry J. Miller, Spring Branch, TX (US)

(73) Assignee: Vidacare Corporation, Shavano Park, TX (US)

( * ) Notice: Subject to any disclaimer, the term of this patent is extended or adjusted under 35 U.S.C. 154(b) by 343 days.

(21) Appl. No.: 12/905,659

(22) Filed: Oct. 15, 2010

(65) Prior Publication Data

US 2011/0028976 A1 Feb. 3, 2011

Related U.S. Application Data

(66) Continuation of application No. 11/064,156, filed on Feb. 23, 2005, now Pat. No. 7,815,642, and a (Continued)

(51) Int. Cl.
*A61B 17/00* (2006.01)
*A61B 17/32* (2006.01)
(Continued)

(52) U.S. Cl.
CPC .......... *A61B 17/3472* (2013.01); *A61B 10/025* (2013.01); *A61B 17/32002* (2013.01); *A61B 17/32053* (2013.01); *A61B 17/3476* (2013.01); *A61B 10/0283* (2013.01); *A61B 17/0642* (2013.01); *A61B 17/068* (2013.01); *A61B 17/1637* (2013.01); *A61B 19/201* (2013.01); *A61B 19/34* (2013.01); *A61B 2010/0258* (2013.01); *A61B 2017/00398* (2013.01); *A61B 2017/0046* (2013.01); *A61B 2017/00734* (2013.01); *A61B 2017/925* (2013.01); *A61B 2019/4868* (2013.01); *A61B 2217/005* (2013.01); *A61M 5/158* (2013.01); *A61M 2005/1581* (2013.01); *A61M 2005/1585* (2013.01); *A61M 2210/02* (2013.01)
USPC .............................. 606/79; 606/182; 604/136

(58) Field of Classification Search
USPC .............. 604/136, 158, 164.01, 272; 606/79, 606/179, 182
See application file for complete search history.

(56) References Cited

U.S. PATENT DOCUMENTS

| 1,539,637 A | 5/1925 | Bronner |
| 2,317,648 A | 4/1943 | Siqveland ...................... 32/26 |

(Continued)

FOREIGN PATENT DOCUMENTS

| CA | 2138842 | 6/1996 | ............ A61M 19/00 |
| CA | 2 454 600 | 1/2004 | ............ A61B 10/00 |

(Continued)

OTHER PUBLICATIONS

International Preliminary Report on Patentability, PCT/US2007/072202, 10 pages, Mailed Jan. 15, 2009.

(Continued)

*Primary Examiner* — Nathan R Price
(74) *Attorney, Agent, or Firm* — Fulbright & Jaworski LLP

(57) ABSTRACT

An apparatus for penetrating a bone marrow of a bone is provided. The apparatus includes a housing comprising a handle and a trigger mechanism, a spring-loaded assembly comprising a rod and a shaft; and a connector comprising a first end operable to connect to the drive shaft and a second end operable to attach to a penetrator hub. The penetrator hub includes a penetrator operable to access the bone marrow.

20 Claims, 4 Drawing Sheets

Related U.S. Application Data continuation-in-part of application No. 11/042,912, filed on Jan. 25, 2005, now Pat. No. 8,641,715, Substitute for application No. 60/539,171, filed on Jan. 26, 2004.

(60) Provisional application No. 60/547,868, filed on Feb. 26, 2004.

(51) Int. Cl.
| | | |
|---|---|---|
| A61M 5/20 | (2006.01) | |
| A61B 17/34 | (2006.01) | |
| A61B 10/02 | (2006.01) | |
| A61B 17/3205 | (2006.01) | |
| A61B 17/064 | (2006.01) | |
| A61B 17/068 | (2006.01) | |
| A61B 17/16 | (2006.01) | |
| A61B 19/00 | (2006.01) | |
| A61B 17/92 | (2006.01) | |
| A61M 5/158 | (2006.01) | |

(56) References Cited

U.S. PATENT DOCUMENTS

| | | | |
|---|---|---|---|
| 2,419,045 A | 4/1947 | Whittaker | 128/305 |
| 2,773,501 A | 12/1956 | Young | 128/221 |
| 3,104,448 A | 9/1963 | Morrow et al. | |
| 3,120,845 A | 2/1964 | Horner | 128/310 |
| 3,173,417 A | 3/1965 | Horner | 128/305 |
| 3,175,554 A | 3/1965 | Stewart | 128/2 |
| 3,507,276 A | 4/1970 | Burgess et al. | 128/173 |
| 3,543,966 A | 12/1970 | Ryan et al. | 222/94 |
| 3,815,605 A | 6/1974 | Schmidt et al. | 128/305 |
| 3,835,860 A | 9/1974 | Garretson | 128/310 |
| 3,893,445 A | 7/1975 | Hofsess | 128/2 |
| 3,991,765 A | 11/1976 | Cohen | 128/305 |
| 4,021,920 A | 5/1977 | Kirschner et al. | 32/28 |
| 4,099,518 A | 7/1978 | Baylis et al. | 600/567 |
| 4,124,026 A | 11/1978 | Berner et al. | 128/303 R |
| 4,142,517 A | 3/1979 | Stavropoulos et al. | 128/2 B |
| 4,170,993 A | 10/1979 | Alvarez | 128/214 R |
| 4,185,619 A | 1/1980 | Reiss | 128/1.1 |
| 4,194,505 A | 3/1980 | Schmitz | 128/218 |
| 4,258,722 A | 3/1981 | Sessions et al. | 128/753 |
| 4,262,676 A | 4/1981 | Jamshidi | 128/753 |
| 4,306,570 A | 12/1981 | Matthews | 128/754 |
| 4,333,459 A | 6/1982 | Becker | 128/218 F |
| 4,381,777 A | 5/1983 | Garnier | 604/188 |
| 4,441,563 A | 4/1984 | Walton, II | 173/163 |
| 4,469,109 A | 9/1984 | Mehl | 128/753 |
| 4,484,577 A | 11/1984 | Sackner et al. | 128/203.28 |
| 4,543,966 A | 10/1985 | Islam et al. | 128/754 |
| 4,553,539 A | 11/1985 | Morris | 128/132 D |
| 4,578,064 A | 3/1986 | Sarnoff et al. | 604/191 |
| 4,605,011 A | 8/1986 | Naslund | 128/752 |
| 4,620,539 A | 11/1986 | Andrews et al. | 128/303 |
| 4,646,731 A | 3/1987 | Brower | 128/156 |
| 4,654,492 A | 3/1987 | Koerner et al. | 200/153 P |
| 4,655,226 A | 4/1987 | Lee | 128/754 |
| 4,659,329 A | 4/1987 | Annis | 604/180 |
| 4,692,073 A | 9/1987 | Martindell | 408/239 A |
| 4,711,636 A | 12/1987 | Bierman | 604/180 |
| 4,713,061 A | 12/1987 | Tarello et al. | 604/200 |
| 4,716,901 A | 1/1988 | Jackson et al. | 128/343 |
| 4,762,118 A | 8/1988 | Lia et al. | 128/4 |
| 4,772,261 A | 9/1988 | Von Hoff et al. | 604/51 |
| 4,787,893 A | 11/1988 | Villette | 604/188 |
| 4,793,363 A | 12/1988 | Ausherman et al. | 128/754 |
| 4,867,158 A | 9/1989 | Sugg | 128/305.1 |
| 4,919,146 A | 4/1990 | Rhinehart et al. | 128/752 |
| 4,921,013 A | 5/1990 | Spalink et al. | 137/614.05 |
| 4,935,010 A | 6/1990 | Cox et al. | 604/122 |
| 4,940,459 A | 7/1990 | Noce | 604/98 |
| 4,944,677 A | 7/1990 | Alexandre | 433/165 |
| 4,969,870 A | 11/1990 | Kramer et al. | 604/51 |
| 5,002,546 A | 3/1991 | Romano | 606/80 |
| 5,025,797 A | 6/1991 | Baran | 128/754 |
| 5,036,860 A | 8/1991 | Leigh et al. | 128/754 |
| 5,057,085 A | 10/1991 | Kopans | 604/173 |
| 5,074,311 A | 12/1991 | Hasson | 128/754 |
| 5,116,324 A | 5/1992 | Brierley et al. | 604/180 |
| 5,120,312 A | 6/1992 | Wigness et al. | 604/175 |
| 5,122,114 A | 6/1992 | Miller et al. | 604/49 |
| 5,137,518 A | 8/1992 | Mersch | 604/168 |
| 5,139,500 A | 8/1992 | Schwartz | 606/96 |
| RE34,056 E | 9/1992 | Lindgren et al. | 128/754 |
| 5,145,369 A | 9/1992 | Lustig et al. | 433/118 |
| 5,172,701 A | 12/1992 | Leigh | 128/753 |
| 5,172,702 A | 12/1992 | Leigh et al. | 128/754 |
| 5,176,643 A | 1/1993 | Kramer et al. | 604/135 |
| 5,195,985 A | 3/1993 | Hall | 604/195 |
| 5,203,056 A | 4/1993 | Funk et al. | 24/543 |
| 5,207,697 A | 5/1993 | Carusillo et al. | 606/167 |
| 5,249,583 A | 10/1993 | Mallaby | 128/754 |
| 5,257,632 A | 11/1993 | Turkel et al. | 128/754 |
| 5,269,785 A | 12/1993 | Bonutti | 606/80 |
| 5,279,306 A | 1/1994 | Mehl | 128/753 |
| 5,312,364 A | 5/1994 | Jacobs | 604/180 |
| 5,324,300 A | 6/1994 | Elias et al. | 606/180 |
| 5,332,398 A | 7/1994 | Miller et al. | 604/175 |
| 5,333,790 A | 8/1994 | Christopher | 239/391 |
| 5,341,823 A | 8/1994 | Manosalva et al. | 128/898 |
| 5,348,022 A | 9/1994 | Leigh et al. | 128/753 |
| 5,357,974 A | 10/1994 | Baldridge | 128/754 |
| 5,368,046 A | 11/1994 | Scarfone et al. | 128/754 |
| 5,372,583 A | 12/1994 | Roberts et al. | 604/51 |
| 5,383,859 A | 1/1995 | Sewell, Jr. | 604/164 |
| 5,385,553 A | 1/1995 | Hart et al. | 604/167 |
| 5,400,798 A | 3/1995 | Baran | 128/754 |
| 5,405,348 A | 4/1995 | Anspach et al. | 606/80 |
| 5,405,362 A | 4/1995 | Kramer et al. | 607/5 |
| 5,423,824 A | 6/1995 | Akerfeldt et al. | 606/80 |
| 5,431,655 A | 7/1995 | Melker et al. | 606/79 |
| 5,451,210 A | 9/1995 | Kramer et al. | 604/137 |
| 5,484,442 A | 1/1996 | Melker et al. | 606/79 |
| D369,858 S | 5/1996 | Baker et al. | D24/112 |
| 5,514,097 A | 5/1996 | Knauer | 604/136 |
| 5,526,821 A | 6/1996 | Jamshidi | 128/753 |
| 5,529,580 A | 6/1996 | Kusunoki et al. | 606/170 |
| 5,549,565 A | 8/1996 | Ryan et al. | 604/167 |
| 5,554,154 A | 9/1996 | Rosenberg | 606/80 |
| 5,556,399 A | 9/1996 | Huebner | 606/80 |
| 5,558,737 A | 9/1996 | Brown et al. | 156/172 |
| 5,571,133 A | 11/1996 | Yoon | 606/185 |
| 5,586,847 A | 12/1996 | Mattern et al. | 408/239 A |
| 5,591,188 A | 1/1997 | Waisman | 606/182 |
| 5,595,186 A | 1/1997 | Rubinstein et al. | 128/754 |
| 5,601,559 A | 2/1997 | Melker et al. | 606/79 |
| 5,632,747 A | 5/1997 | Scarborough et al. | 606/79 |
| 5,672,155 A | 9/1997 | Riley et al. | 604/154 |
| 5,713,368 A | 2/1998 | Leigh | 128/753 |
| 5,724,873 A | 3/1998 | Hillinger | 81/451 |
| 5,733,262 A | 3/1998 | Paul | 604/116 |
| 5,752,923 A | 5/1998 | Terwilliger | 600/562 |
| 5,762,639 A | 6/1998 | Gibbs | 604/272 |
| 5,766,221 A | 6/1998 | Benderev et al. | 606/232 |
| 5,769,086 A | 6/1998 | Ritchart et al. | 128/753 |
| 5,779,708 A | 7/1998 | Wu | 606/80 |
| 5,800,389 A | 9/1998 | Burney et al. | 604/93 |
| 5,807,277 A | 9/1998 | Swaim | 600/567 |
| 5,810,826 A | 9/1998 | Akerfeldt et al. | 606/80 |
| 5,817,052 A | 10/1998 | Johnson et al. | 604/51 |
| 5,823,970 A | 10/1998 | Terwilliger | 600/564 |
| D403,405 S | 12/1998 | Terwilliger | D24/130 |
| 5,858,005 A | 1/1999 | Kriesel | 604/180 |
| 5,868,711 A | 2/1999 | Kramer et al. | 604/136 |
| 5,868,750 A | 2/1999 | Schultz | 606/104 |
| 5,873,499 A | 2/1999 | Leschinsky et al. | 222/327 |
| 5,873,510 A | 2/1999 | Hirai et al. | 227/130 |
| 5,885,226 A | 3/1999 | Rubinstein et al. | 600/564 |
| 5,891,085 A | 4/1999 | Lilley et al. | 604/68 |
| 5,911,701 A | 6/1999 | Miller et al. | 604/22 |
| 5,911,708 A | 6/1999 | Teirstein | 604/183 |

(56) References Cited

U.S. PATENT DOCUMENTS

| | | | |
|---|---|---|---|
| 5,916,229 A | 6/1999 | Evans | 606/171 |
| 5,919,172 A | 7/1999 | Golba, Jr. | 604/272 |
| 5,924,864 A | 7/1999 | Loge et al. | 433/118 |
| 5,927,976 A | 7/1999 | Wu | 433/82 |
| 5,928,238 A | 7/1999 | Scarborough et al. | 606/79 |
| 5,941,706 A | 8/1999 | Ura | 433/165 |
| 5,941,851 A | 8/1999 | Coffey et al. | 604/131 |
| 5,951,026 A | 9/1999 | Harman et al. | 279/143 |
| 5,960,797 A | 10/1999 | Kramer et al. | 128/899 |
| 5,980,545 A | 11/1999 | Pacala et al. | 606/170 |
| 5,993,417 A | 11/1999 | Yerfino et al. | 604/110 |
| 5,993,454 A | 11/1999 | Longo | 606/80 |
| 6,007,496 A | 12/1999 | Brannon | 600/565 |
| 6,017,348 A | 1/2000 | Hart et al. | 606/79 |
| 6,018,094 A | 1/2000 | Fox | 623/11 |
| 6,022,324 A | 2/2000 | Skinner | 600/566 |
| 6,027,458 A | 2/2000 | Janssens | 600/567 |
| 6,033,369 A | 3/2000 | Goldenberg | 600/567 |
| 6,033,411 A | 3/2000 | Preissman | 606/99 |
| 6,042,585 A | 3/2000 | Norman | 606/104 |
| 6,063,037 A | 5/2000 | Mittermeier et al. | 600/567 |
| 6,071,284 A | 6/2000 | Fox | 606/80 |
| 6,080,115 A | 6/2000 | Rubinstein et al. | 600/567 |
| 6,083,176 A | 7/2000 | Terwilliger | 600/562 |
| 6,086,543 A | 7/2000 | Anderson et al. | 600/567 |
| 6,086,544 A | 7/2000 | Hibner et al. | 600/568 |
| 6,096,042 A | 8/2000 | Herbert | 606/80 |
| 6,102,915 A | 8/2000 | Bresler et al. | 606/80 |
| 6,106,484 A | 8/2000 | Terwilliger | 600/568 |
| 6,110,128 A | 8/2000 | Andelin et al. | 600/566 |
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,135,769 A | 10/2000 | Kwan | 433/80 |
| 6,159,163 A | 12/2000 | Strauss et al. | 600/566 |
| 6,162,203 A | 12/2000 | Haaga | 604/272 |
| 6,183,442 B1 | 2/2001 | Athanasiou et al. | 604/154 |
| 6,210,376 B1 | 4/2001 | Grayson | 604/264 |
| 6,217,561 B1 | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,238,355 B1 | 5/2001 | Daum | 600/567 |
| 6,247,928 B1 | 6/2001 | Meller et al. | 433/80 |
| 6,248,110 B1 | 6/2001 | Reiley et al. | 606/93 |
| 6,257,351 B1 | 7/2001 | Ark et al. | 173/178 |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming et al. | 600/567 |
| 6,309,358 B1 | 10/2001 | Okubo | 600/466 |
| 6,312,394 B1 | 11/2001 | Fleming | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdoff et al. | 600/568 |
| 6,443,910 B1 | 9/2002 | Krueger et al. | 600/567 |
| 6,468,248 B1 | 10/2002 | Gibbs | 604/164.01 |
| 6,478,751 B1 | 11/2002 | Krueger et al. | 600/566 |
| 6,488,636 B2 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | 606/80 |
| 6,540,694 B1 | 4/2003 | Van Bladel et al. | 600/564 |
| 6,547,511 B1 | 4/2003 | Adams | 414/46.4 |
| 6,547,561 B2 | 4/2003 | Meller et al. | 433/80 |
| 6,550,786 B2 | 4/2003 | Gifford et al. | 279/75 |
| 6,554,779 B2 | 4/2003 | Viola et al. | 600/568 |
| 6,555,212 B2 | 4/2003 | Boiocchi et al. | 428/295.4 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stehens et al. | 600/567 |
| 6,626,848 B2 | 9/2003 | Nueenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,884,245 B2 | 4/2005 | Spranza | 606/79 |
| 6,887,209 B2 | 5/2005 | Kadziauskas et al. | 600/565 |
| 6,890,308 B2 | 5/2005 | Islam | 600/564 |
| 6,905,486 B2 | 6/2005 | Gibbs | 604/510 |
| 6,930,461 B2 | 8/2005 | Ruthowski | 318/567 |
| 6,942,669 B2 | 9/2005 | Kurc | 606/80 |
| 6,969,373 B2 | 11/2005 | Schwartz et al. | 604/170.03 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,025,732 B2 | 4/2006 | Thompson et al. | 600/654 |
| 7,063,672 B2 | 6/2006 | Schramm | 600/564 |
| 7,137,985 B2 | 11/2006 | Jahng | 606/61 |
| 7,207,949 B2 | 4/2007 | Miles et al. | 600/554 |
| 7,226,450 B2 | 6/2007 | Athanasiou et al. | 606/80 |
| 7,229,401 B2 | 6/2007 | Kindlein | 600/7 |
| 7,670,328 B2 | 3/2010 | Miller | 604/506 |
| 7,699,850 B2 | 4/2010 | Miller | 606/80 |
| 7,811,260 B2 | 10/2010 | Miller et al. | 604/188 |
| 7,815,642 B2 | 10/2010 | Miller | 606/79 |
| 7,850,620 B2 | 12/2010 | Miller et al. | 600/568 |
| 7,951,089 B2 | 5/2011 | Miller | 600/566 |
| 8,038,664 B2 | 10/2011 | Miller et al. | 604/506 |
| 8,419,683 B2 | 4/2013 | Miller et al. | 604/117 |
| 8,480,632 B2 | 7/2013 | Miller et al. | 604/188 |
| 8,506,568 B2 | 8/2013 | Miller | 606/80 |
| 8,641,715 B2 | 2/2014 | Miller | 606/80 |
| 8,656,929 B2 | 2/2014 | Miller et al. | 128/898 |
| 8,668,698 B2 | 3/2014 | Miller | 606/80 |
| 8,684,978 B2 | 4/2014 | Miller | 604/235 |
| 8,690,791 B2 | 4/2014 | Miller | 600/562 |
| 8,715,287 B2 | 5/2014 | Miller | 606/80 |
| 2001/0005778 A1 | 6/2001 | Ouchi | 600/564 |
| 2001/0014439 A1 | 8/2001 | Meller et al. | 466/50 |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |

(56) References Cited

U.S. PATENT DOCUMENTS

| | | | |
|---|---|---|---|
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | 606/80 |
| 2004/0019297 A1 | 1/2004 | Angel | 600/564 |
| 2004/0019299 A1 | 1/2004 | Richart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | 600/564 |
| 2004/0092946 A1 | 5/2004 | Bagga et al. | 606/93 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | 600/562 |
| 2004/0220497 A1 | 11/2004 | Findlay et al. | 600/562 |
| 2005/0027210 A1 | 2/2005 | Miller | 600/567 |
| 2005/0040060 A1 | 2/2005 | Anderson et al. | 206/363 |
| 2005/0075581 A1 | 4/2005 | Schwindt | 600/568 |
| 2005/0085838 A1 | 4/2005 | Thompson et al. | 606/170 |
| 2005/0101880 A1 | 5/2005 | Cicenas et al. | 600/567 |
| 2005/0113716 A1 | 5/2005 | Mueller, Jr. et al. | 600/568 |
| 2005/0124915 A1 | 6/2005 | Eggers et al. | 600/568 |
| 2005/0131345 A1 | 6/2005 | Miller | 604/117 |
| 2005/0148940 A1 | 7/2005 | Miller | 604/187 |
| 2005/0165328 A1 | 7/2005 | Heske et al. | 600/566 |
| 2005/0165403 A1 | 7/2005 | Miller | 606/79 |
| 2005/0165404 A1 | 7/2005 | Miller | 606/80 |
| 2005/0171504 A1 | 8/2005 | Miller | 604/164 |
| 2005/0182394 A1 | 8/2005 | Spero et al. | 606/21 |
| 2005/0200087 A1 | 9/2005 | Vasudeva et al. | 279/143 |
| 2005/0203439 A1 | 9/2005 | Heske et al. | 600/566 |
| 2005/0209530 A1 | 9/2005 | Pflueger | 600/567 |
| 2005/0215921 A1 | 9/2005 | Hibner et al. | 600/566 |
| 2005/0228309 A1 | 10/2005 | Fisher et al. | 600/562 |
| 2005/0261693 A1 | 11/2005 | Miller et al. | 606/80 |
| 2006/0011506 A1 | 1/2006 | Riley | 206/570 |
| 2006/0015066 A1 | 1/2006 | Turieo et al. | 604/136 |
| 2006/0036212 A1 | 2/2006 | Miller | 604/48 |
| 2006/0052790 A1 | 3/2006 | Miller | 606/80 |
| 2006/0074345 A1 | 4/2006 | Hibner | 600/566 |
| 2006/0079774 A1 | 4/2006 | Anderson | 600/442 |
| 2006/0089565 A1 | 4/2006 | Schramm | 600/568 |
| 2006/0122535 A1 | 6/2006 | Daum | 600/565 |
| 2006/0129082 A1 | 6/2006 | Rozga | 604/6.04 |
| 2006/0144548 A1 | 7/2006 | Beckman et al. | 163/1 |
| 2006/0149163 A1 | 7/2006 | Hibner et al. | 600/566 |
| 2006/0167377 A1 | 7/2006 | Richart et al. | 600/566 |
| 2006/0167378 A1 | 7/2006 | Miller | 600/566 |
| 2006/0167379 A1 | 7/2006 | Miller | 600/566 |
| 2006/0184063 A1 | 8/2006 | Miller | 600/568 |
| 2006/0189940 A1 | 8/2006 | Kirsch | 604/164.1 |
| 2007/0016100 A1 | 1/2007 | Miller | 600/566 |
| 2007/0049945 A1 | 3/2007 | Miller | 606/86 |
| 2007/0149920 A1 | 6/2007 | Michels et al. | 604/93.01 |
| 2007/0213735 A1 | 9/2007 | Sandat et al. | 606/79 |
| 2007/0270775 A1 | 11/2007 | Miller et al. | 604/506 |
| 2008/0015467 A1 | 1/2008 | Miller | 600/568 |
| 2008/0015468 A1 | 1/2008 | Miller | 600/568 |
| 2008/0045857 A1 | 2/2008 | Miller | 600/566 |
| 2008/0045860 A1 | 2/2008 | Miller et al. | 600/567 |
| 2008/0045861 A1 | 2/2008 | Miller et al. | 600/567 |
| 2008/0045965 A1 | 2/2008 | Miller et al. | 606/80 |
| 2008/0140014 A1 | 6/2008 | Miller et al. | 604/180 |
| 2008/0215056 A1 | 9/2008 | Miller et al. | 606/80 |
| 2008/0221580 A1 | 9/2008 | Miller et al. | 606/80 |

FOREIGN PATENT DOCUMENTS

| | | | |
|---|---|---|---|
| CN | 2320209 | 5/1999 | |
| CN | 2664675 | 12/2004 | |
| DE | 10057931 A1 | 11/2000 | A61B 17/32 |
| EP | 517000 | 12/1992 | A61M 5/168 |
| EP | 0807412 | 11/1997 | |
| EP | 0807412 A1 | 11/1997 | A61B 17/32 |
| EP | 1099450 | 5/2001 | A61M 5/32 |
| EP | 1447050 | 5/2001 | |
| EP | 1314452 | 5/2003 | |
| EP | 1421907 | 5/2004 | |
| FR | 853349 | 3/1940 | |
| FR | 2457105 | 5/1979 | A61M 5/00 |
| FR | 2516386 | 11/1981 | A61M 5/18 |
| GB | 2130890 | 6/1984 | A61B 10/00 |
| JP | 59119808 | 7/1984 | |
| JP | 1052433 | 2/1989 | A61B 1/00 |
| JP | 6132663 | 5/1994 | |
| JP | 2001505076 | 4/2001 | |
| WO | WO 92/08410 | 5/1992 | |
| WO | 9307819 | 4/1993 | A61B 17/32 |
| WO | 9631164 | 10/1996 | A61B 17/34 |
| WO | 9806337 | 2/1998 | A61B 17/16 |
| WO | WO 98/52638 | 11/1998 | |
| WO | 99/18866 | 4/1999 | A61B 17/34 |
| WO | 9952444 | 10/1999 | A61B 17/00 |
| WO | WO 00/09024 | 2/2000 | |
| WO | 00/56220 | 9/2000 | A61B 10/00 |
| WO | 01/78590 | 10/2001 | A61B 5/00 |
| WO | 0241792 | 5/2002 | A61B 17/16 |
| WO | 2417921 | 5/2002 | A61B 17/16 |
| WO | 02096497 | 12/2002 | A61M 31/00 |
| WO | WO 03/015637 | 2/2003 | |
| WO | WO 2005/072625 | 8/2005 | |
| WO | 2005110259 | 11/2005 | A61B 17/88 |
| WO | 2005112800 | 12/2005 | A61B 17/34 |
| WO | WO 2008-033874 | 3/2008 | |
| WO | 2008081438 | 7/2008 | |
| WO | WO 2011-123703 | 10/2011 | |

OTHER PUBLICATIONS

International Preliminary Report on Patentability, PCT/US2007/072217, 11 pages, Mailed Feb. 12, 2009.

Official Action for European Application No. 03756317.8 (4 pages), Mailed Dec. 28, 2006.

Invitation to Pay Additional Fees for Application No. PCT/US2006/025201 (6 pages), Mailed Oct. 26, 2006.

Australian Exam Report on Patent Application No. 2003240970, 2 pages, Oct. 15, 2007.

Official Action for European Application No. 03756317.8 (4 pages), Dec. 28, 2006.

International Search Report and Written Opinion for International Application No. PCT/US2006/025201 (18 pages), Jan. 29, 2007.

International Search Report, PCT/US2007/072209, 9 pages, Mailing Date Mar. 12, 2007.

International Search Report, PCT/US2007/072217, 9 pages, Mailing Date Mar. 12, 2007.

Preliminary Report on Patentability, PCT/US2006/025201, 12 pages, Mailing Date Feb. 7, 2008.

Gunal et al., Compartment Syndrome After Intraosseous Infusion: An Expirmental Study in Dogs, Journal od Pediatric Surgery, vol. 31, No. 11, pp. 1491-1493, Nov. 1996.

International Search Report, PCT/US2007/072217, 20 pages, Mailing Date Mar. 31, 2008.

International Search Report, PCT/US2007/072209, 18 pages, Mailing Date Apr. 25, 2008.

Communication Pursuant to Article 94(3) EPC, Application No. 05 712 091.7-1265, 4 pages, Apr. 8, 2008.

Notification of the Chinese Office Action, Application No. 200580003261.81, 3 pages, Mar. 1, 2008.

International Search Report and Written Opinion, PCT/US08/500346, 12 pages, Mailing Date May 22, 2008.

Chinese Office Action, Application No. 2005800003261, (with English translation), (9 pgs), Jan. 16, 2009.

(56) References Cited

OTHER PUBLICATIONS

Japanese Office Action, Application No. 2004-508,670, (with English summary), (13 pgs), Apr. 21, 2009.
PCT Preliminary Report on Patentability, PCT/US/2008/050346, (8 pgs), Jul. 23, 2009.
European Office Action and Search Report, Application No. 09150973.7, 8 pages, Oct. 23, 2009.
International Preliminary Report on Patentability, PCT/US08/52943, 7 pages, Mailed Oct. 15, 2009.
Japanese Office Action, Application No. 2004-508,669, (with English summary), (9 pgs), Aug. 3, 2009.
Chinese Office Action, Application No. 200780000590.6, (with English translation), (13 pgs), Aug. 21, 2009.
International Preliminary Report on Patentability PCT/US2005/002484, 9 pages, Mailed Aug. 3, 2006.
International PCT Search Report and Written Opinion PCT/US2004/037753, 16 pages, Mailed Jul. 8, 2005.
International PCT Search Report and Written Opinion PCT/US2005/002484, 15 pages, Mailed Jul. 22, 2005.
International Preliminary Report on Patentability, PCT/US/2007/078203, 13 pages, Mar. 26, 2009.
International Preliminary Report on Patentability, PCT/US/2007/078207, 10 pages, Mar. 26, 2009.
International Preliminary Report on Patentability, PCT/US/2007/078205, 10 pages, Mar. 26, 2009.
International Preliminary Report on Patentability, PCT/US/2007/078204, 11 pages, Apr. 2, 2009.
Vidacare Corporation Comments to Intraosseous Vascular Access Position Paper, Infusion Nurses Society, 6 pages, May 4, 2009.
International Preliminary Report on Patentability, PCT/US/2007/072209, 10 pages, May 14, 2009.
Communication relating to the results of the partial International Search Report for PCT/US2005/002484, 6 pages, Mailed May 19, 2005.
Richard O. Cummings et al., "ACLS—Principles and Practice", ACLS—The Reference Textbook, American Heart Association, pp. 214-218, 2003.
International PCT Search Report, PCT/US03/17167, 8 Pages, Mailed Sep. 16, 2003.
International PCT Search Report, PCT/US03/17203, 8 Pages, Mailed Sep. 16, 2003
International PCT Search Report PCT/US2004/037753, 6 Pages, Mailed Apr. 19, 2005.
Åström, K.G., "Automatic Biopsy Instruments Used Through a Coaxial Bone Biopsy System with an Eccentric Drill Tip," Acta Radiologica, 1995; 36:237-242, May 1995.
Åström, K. Gunnar O., "CT-guided Transsternal Core Biopsy of Anterior Mediastinal Masses," Radiology 1996; 199:564-567, May 1996.
International PCT Search Report PCT/US03/17167, 8 pages, Mailed Sep. 16, 2003.
International PCT Search Report PCT/US03/17203, 8 pages, Mailed Sep. 16, 2003.
Cummins, Richard O., et al, "ACLS—Principles and Practice", ACLS—The Reference Textbook, American Heart Association, pp. 214-218, 2003.
Riley et al., "A Pathologist's Perspective on Bone Marrow Aspiration Biopsy: I. Performing a Bone Marrow Examination," Journal of Clinical Laboratory Analysis 18, pp. 70-90, 2004
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.

Liakat A. Parapia, Trepanning or trephines: a history of bone marrow biopsy, British Journal of Haematology, pp. 14-19 2007.
Pediatric Emergency, Intraosseous Infusion for Administration of Fluids and Drugs, www.cookgroup.com, 1 pg, 2000.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
European Search Report 08158699.2-1265, 4 pages, Aug. 2008.
International Search Report and Written Opinion, PCT/US2007/078204, 14 pages, Mailing Date May 15, 2008.
International Search Report and Written Opinion, PCT/US08/52943, 8 pages, Mailing Date Sep. 26, 2008.
European Office Action Communication, Application No. 08158699.2-1265/1967142, 10 pages, Nov. 4, 2008.
PCT Invitation to Pay Additional Fees, PCT/US2007/072209, 9 pages, Mailing Dec. 3, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
BioAccess.com, Single Use Small Bone Power Tool—How It Works, 1 pg, Printed Jun. 9, 2008.
International Search Report and Written Opinion, PCT/US2007/078203, 15 pages, Mailing Date May 13, 2008.
International Search Report and Written Opinion, PCT/US2007/072202, 17 pages, Mailing Date Mar. 25, 2008.
International Search Report and Written Opinion, PCT/US2007/078207, 13 pages, Mailing Date Apr. 7, 2008.
International Search Report and Written Opinion, PCT/US2007/078205, 13 pages, Mailing date Sep. 11, 2007.
European Office Action EP03731475.4, 4 pages, Oct. 11, 2007.
Liakat A. Parapia, Trepanning or trephines: a history of bone marrow biopsy, British Journal of Haematology, pp. 14-19, 2007.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Chinese Office Action w/english translation; Application No. 200680021872.X; pp. 8, Nov. 6, 2009.
Chinese Office Action with English translation; Application No. 200910006631.3; pp. 12, Mar. 11, 2010.
European Extended Search Report, Application No. EP10153350.3, 5 pages, Mar. 11, 2010.
Taiwan Office Action, Application No. 94102179 (with English translation); 12 pages, May 13, 2010.
Office Action issued in Chinese Application No. 200910006631.3, dated Mar. 22, 2011.
Notice of Allowance issued in U.S. Appl. No. 11/253,467, mailed Mar. 4, 2014.
Notice of Allowance in U.S. Appl. No. 11/620,927 mailed Jun. 3, 2014.
Notice of Allowance in U.S. Appl. No. 12/407,651 mailed Jun. 11, 2014.
International Search Report and Written Opinion in PCT/US2014/028594, mailed Jul. 28, 2014.
Notice of Allowance in U.S. Appl. No. 11/380,340 mailed Aug. 22, 2014.
Notice of Allowance in U.S. Appl. No. 14/721,144 mailed Jul. 22, 2014.
Notice of Allowance in U.S. Appl. No. 11/619,390 mailed Jul. 3, 2014.

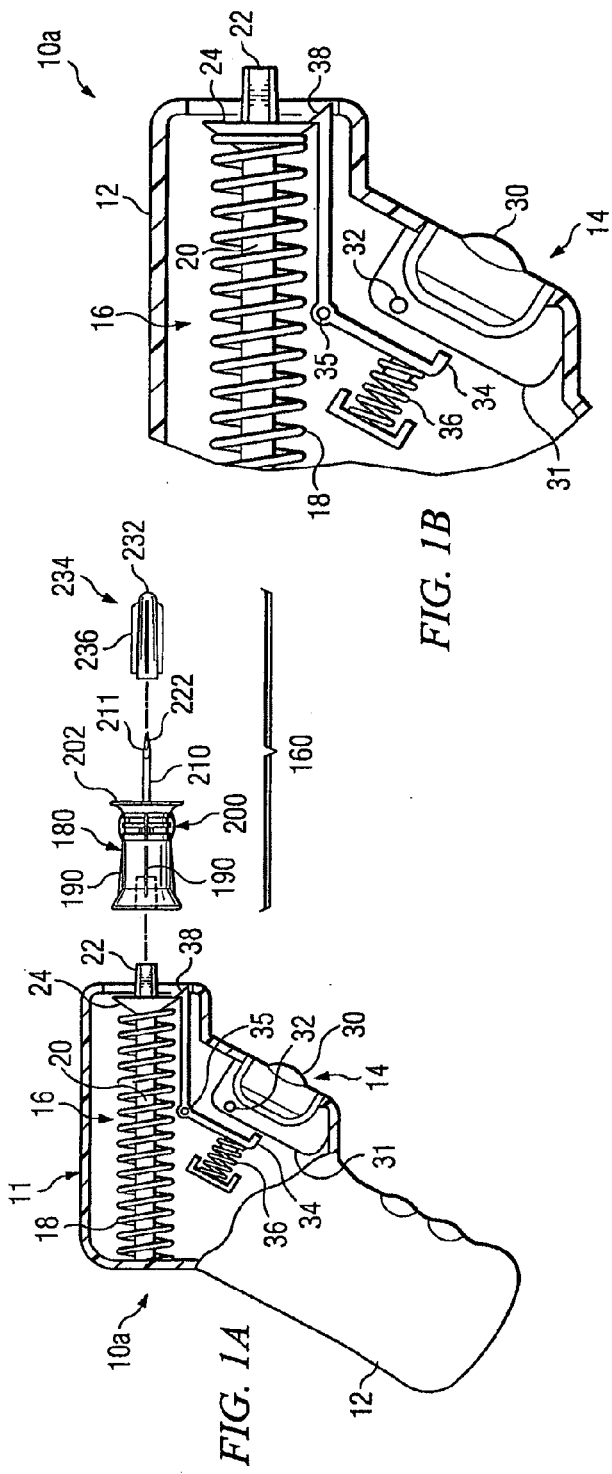
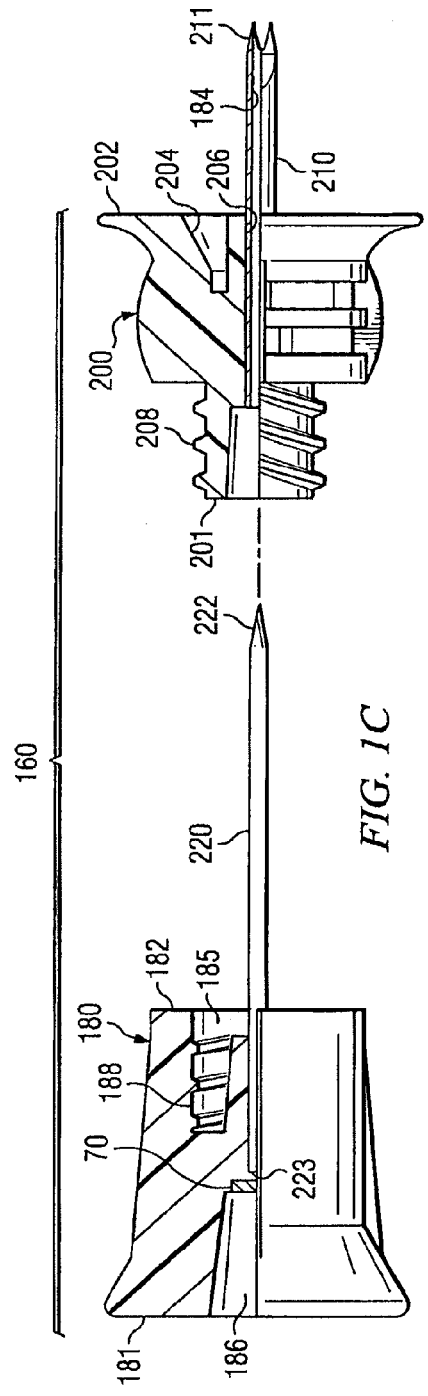
FIG. 1A
FIG. 1B
FIG. 1C

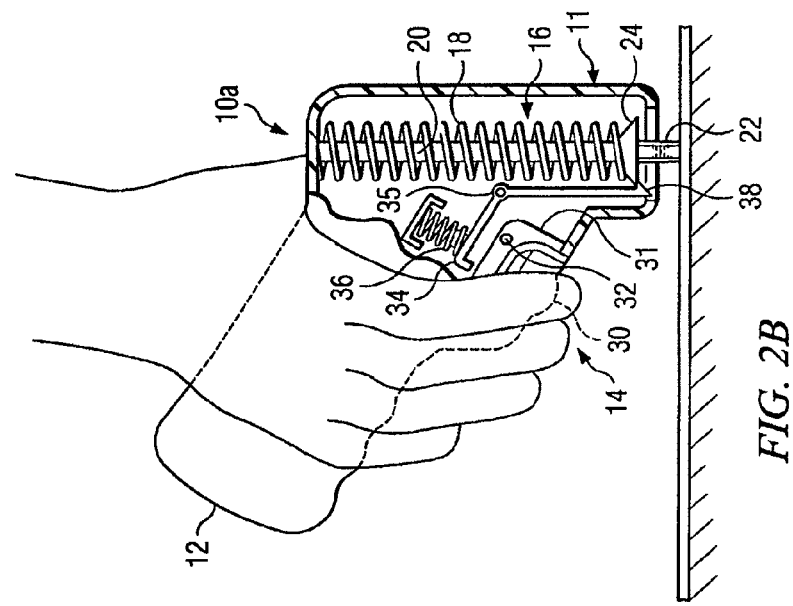
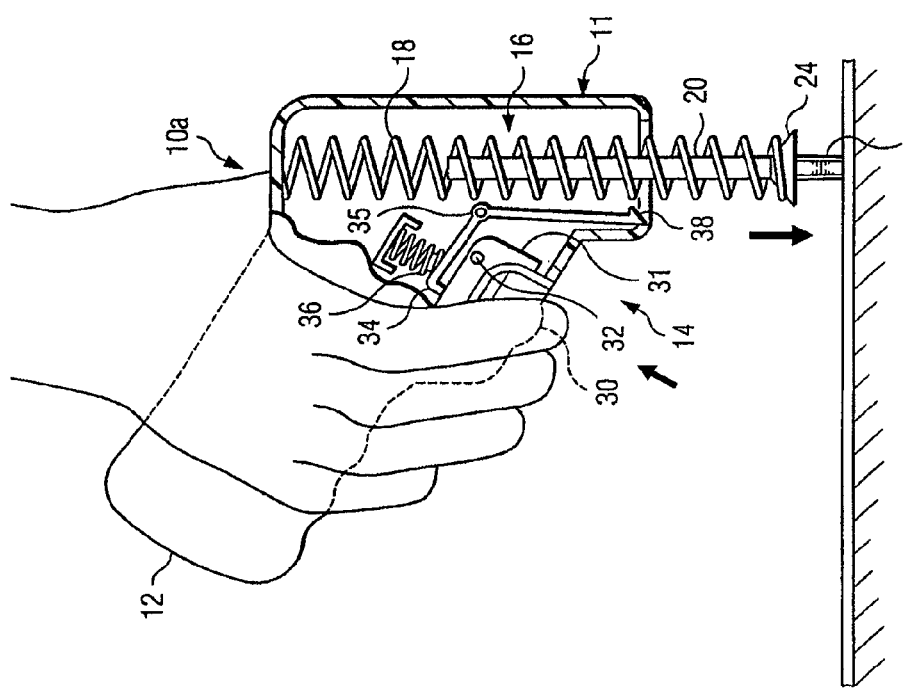

IMPACT-DRIVEN INTRAOSSEOUS NEEDLE

RELATED APPLICATIONS

This application claims the benefit under 35 U.S.C. §120 as a Continuation of U.S. application Ser. No. 11/064,156 filed Feb. 23, 2005, now U.S. Pat. No. 7,815,642 which claims the benefit under 35 U.S.C. §119(e) of U.S. Provisional Patent Application Ser. No. 60/547,868 filed Feb. 26, 2004, and also claims the benefit under 35 U.S.C. §120 as a Continuation-in-Part of U.S. patent application Ser. No. 11/042,912, filed Jan. 25, 2005, now U.S. Pat. No. 8,641,715 which claims the benefit under 35 U.S.C. §119(e) of U.S. Provisional Patent Application Ser. No. 60/539,171 filed Jan. 26, 2004.

TECHNICAL FIELD

The present invention is related in general to a medical device to access the bone marrow of a bone and specifically to an apparatus and method for penetrating the bone marrow and inserting a penetrator or needle.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

SUMMARY OF THE INVENTION

In accordance with teachings of the present invention, an apparatus for penetrating the bone marrow of a bone is provided. The apparatus includes a housing having a handle and a trigger mechanism, a spring-loaded assembly comprising at least one spring, a rod and a shaft, a connector having a first end operable to connect to the shaft and a second end operable to attach to a penetrator hub. The penetrator hub includes a penetrator operable to access the bone marrow.

In an alternate embodiment of the invention, an apparatus for penetrating the bone marrow is provided which includes a housing having a handle and a trigger mechanism, a spring-loaded assembly comprising at least one spring, a rod, a sleeve operable to slide over the rod and a shaft, a connector having a first end operable to connect to the drive shaft and a second end operable to attach to a penetrator hub, the penetrator hub having a penetrator operable to access the bone marrow and a ratchet mechanism comprising a ratchet lever operable to compress the spring.

In another embodiment of the invention a method of accessing the bone marrow of a bone is provided which includes applying an apparatus including a housing having a handle and a trigger mechanism, a spring-loaded assembly having at least one spring, a rod and a shaft, a connector comprising a first end operable to connect to the shaft and a second end operable to attach to a penetrator hub, the penetrator hub having a penetrator operable to access the bone marrow, to a bone overlying bone marrow, activating the trigger mechanism of the apparatus, detaching the apparatus from the connector and detaching the connector from the penetrator hub.

Apparatus and methods incorporating teachings of the present invention may be used to access the bone marrow of any bone in a human or animal's body for any purpose including the delivery of fluids, medications, drugs, chemicals and any other bioactive substances including blood. Teachings of the present invention may also be used for harvesting bone marrow and/or stem cell. Teachings of the present invention may also be used to access body tissue or body cavities other than bone marrow in a human or animal species.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 1A shows an example illustration of an apparatus operable for penetrating the bone marrow of a bone;

FIG. 1B shows an example illustration of a trigger mechanism of an apparatus operable for penetrating the bone marrow of a bone;

FIG. 1C shows an example illustration of a penetrator assembly for penetrating the bone marrow of a bone;

FIG. 2A shows an example illustration of a use of an apparatus operable for penetrating the bone marrow of a bone;

FIG. 2B shows an example illustration of a use of an apparatus operable for penetrating the bone marrow of a bone;

DETAILED DESCRIPTION OF THE INVENTION

Figure 3A:
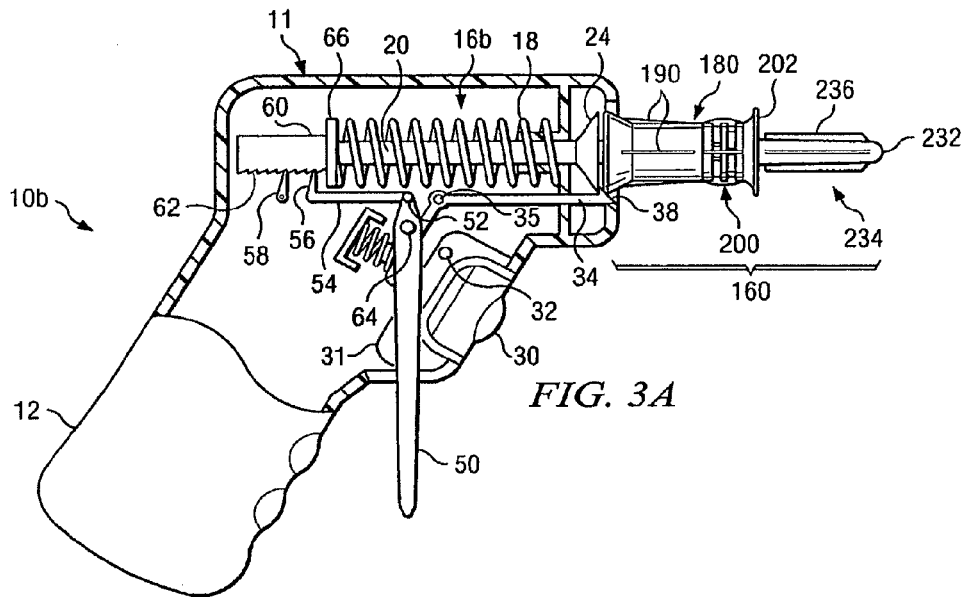
FIG. 3A shows an example illustration of an apparatus operable for penetrating the bone marrow of a bone.

Some preferred embodiments of the invention and its advantages are best understood by reference to FIGS. 1A-4 wherein like numbers refer to same and like parts.

Various aspects of the present invention may be described with respect to treating human patients. However, apparatus and methods incorporating teachings of the present invention may be used to treat veterinary patients as well.

There are times when the availability or advisability of having a battery-powered driver for intraosseous (IO) access is not possible. Such conditions may involve military special operations where extreme temperatures and severe weight restrictions limit what can be carried into battle. The same may be true for civilian emergency medical services (EMS), or first responders, where long shelf life and infrequent use make the convenience of a battery-powered driver impractical. For this reason, an impact-driven device offers certain advantages over a battery-powered driver. Impact-driven technology is analogous to a nail gun, in that stored energy in the form of a compressed spring may be used to propel a bone-penetrating needle into the bone marrow. Once the needle is positioned in the bone marrow it may be used for infusing fluids and drugs into the body. Current impact-driven devices lack the ability to modulate the firing force of the needle, lack an effective safety mechanism and lack a handle which can be firmly grasped and pointed in only one direction, at an intended target.

When an impact-driven device is used, a trigger may be compressed by an operator to activate or fire a spring-loaded mechanism and propel a penetrator or needle into the bone marrow of a bone. An impact-driven device may also serve as a useful backup in cases where a battery-powered driver fails to function, for example, due to a depleted power supply.

FIGS. 1A and 1B show one embodiment of an impact-driven apparatus driver 10a wherein housing 11 includes handle 12 and trigger mechanism 14. Handle 12 may be formed in a variety of shapes, such as a pistol-type grip shown in FIGS. 1A and 1B. A pistol-shaped housing allows apparatus 10a to be grasped in the palm of the hand in an intuitive manner by an operator, i.e. when grasped it can only be fired in one direction, at an intended target. This aspect of the invention is important to prevent inadvertent firing of apparatus 10a. Housing 11 may be formed from materials satisfactory for multiple uses or may be formed from materials satisfactory for one time or disposable use. Other handle shapes (not expressly shown) may also be used with an impact driven device such as a T-shaped handle, or any other ergonomically-designed shape suitable for grasping with the hand or fingers during insertion of a penetrator.

Apparatus 10a includes spring-loaded assembly 16. In one embodiment of the invention, spring-loaded assembly 16 includes spring 18, rod 20 and shaft 22. Spring 18 may be coiled and is configured to surround rod 20. Rod 20 includes a first end and a second end. Second end of rod 20 includes circular protrusion 24 and shaft 22. Circular protrusion 24 holds spring 18 in position and maintains the position of spring 18 on rod 20. Circular protrusion 24 is configured to engage with trigger mechanism 14 described below. Shaft 22 is configured to attach to connector 180. In one embodiment, spring-loaded assembly includes spring 18 which may be configured to surround rod 20. When spring 18 is in a compressed position, as shown in FIG. 1A, apparatus 10a is in a cocked or loaded state, capable of propelling penetrator assembly 160 into the bone marrow of a bone. In alternate embodiments of the invention a spring-loaded mechanism may include one or more springs, a coiled spring, a leaf spring or a bellows (not expressly shown). Shaft 22 as shown in FIG. 1A may have five sides. Corresponding opening 186 as shown in FIG. 1C may also include five sides compatible with releasably receiving drive shaft 22. In other embodiments (not expressly shown), shaft 22 may be substantially round or square or any other shape or configuration suitable for attachment to a connector of a penetrator assembly. Shaft 22 may be magnetized in order to attach to metallic disc 70 embedded in penetrator assembly 160 as shown in FIG. 1C (described below). Other types of connectors may include an O-ring mechanism or a ball and detent mechanism (not expressly shown).

FIG. 1B shows a close-up view of trigger mechanism 14. In one embodiment, trigger mechanism 14 includes trigger button 30 that may be compressed by an operator to release spring-loaded assembly 16 and activate apparatus 10a to propel penetrator assembly 160 into the bone marrow of a bone. For example, as shown in FIG. 1B, compression of trigger button 30 moves trigger plate 31 against adjacent portions of L-shaped bar 34 to compress trigger spring 36 and rotate L-shaped bar 34 relative to pivot pin 35. Rotation of L-shaped bar 34 allows end projection 38 of L-shaped bar 34 to move away from circular protrusion 24 of rod 20 thereby releasing spring 18 of spring-loaded assembly 16 and activating or firing penetrator assembly 160 into the bone marrow of a bone. End projection 38 may be formed as a simple protrusion as shown or it may be configured in the shape of a pawl or clip (not expressly shown). In one embodiment, trigger button 30 may include safety pin hole 32 and an associated safety pin (not expressly shown). When a safety pin is inserted into safety pin hole 32 apparatus 10a cannot be fired thereby avoiding inadvertent firing of apparatus 10a at an unintended target.

Figure 3B:
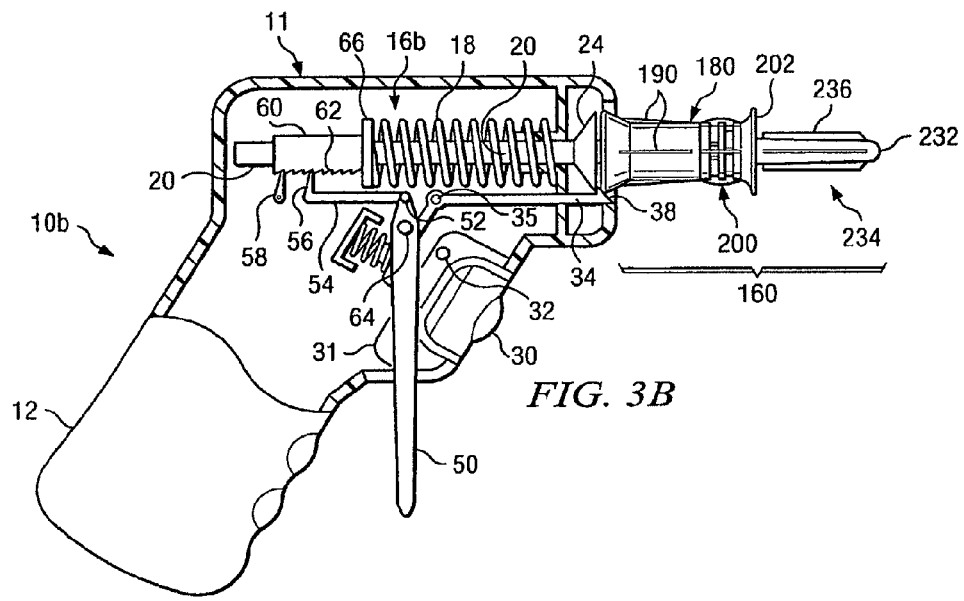
FIG. 3B shows an example illustration of an apparatus operable for penetrating the bone marrow of a bone.
Figure 3C:
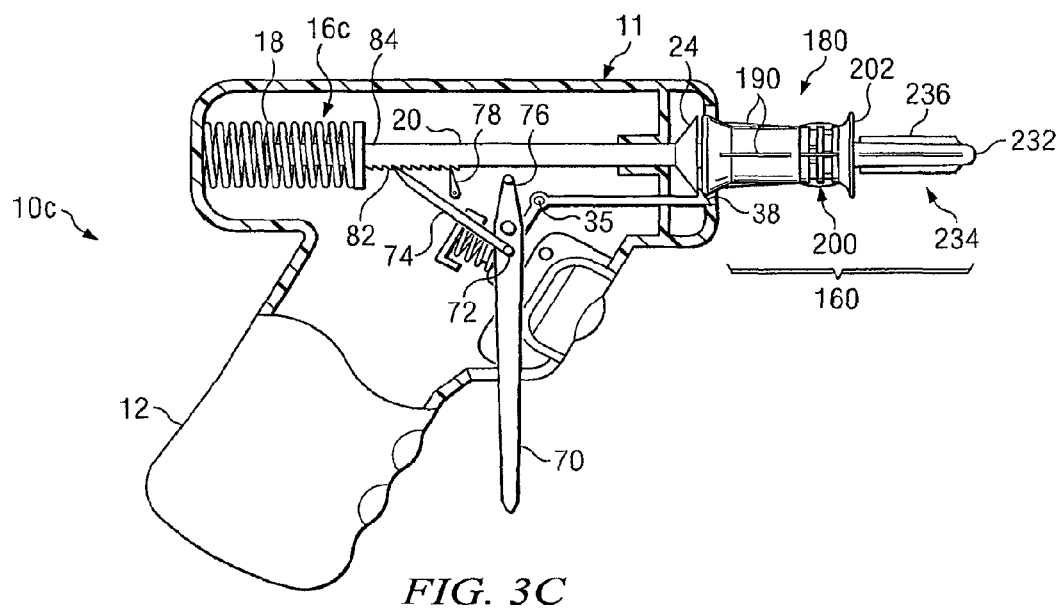
FIG. 3C shows an example illustration of an apparatus operable for penetrating the bone marrow of a bone.

Shaft or attachment 22 may be releasably engaged with end 181 of connector 180 as shown in FIG. 3C. Inner penetrator or trocar 220 extends from end 182 of connector 180. Connector 180 and attached inner penetrator 220 may be releasably engaged with each other by Luer type fittings, threaded connections or other suitable fittings formed on first end 201 of hub 200. Outer penetrator 210 extends from second end 202 of hub 200.

As shown in FIG. 1C, penetrator assembly 160 may include connector 180, and associated hub 200, outer penetrator 210 and inner penetrator 220. Penetrator assembly 160 may include an outer penetrator such as a cannula, hollow tube or hollow drill bit and an inner penetrator such as a stylet or trocar. Various types of stylets and/or trocars may be disposed within an outer penetrator. For some applications outer penetrator or cannula 210 may be described as a generally elongated tube sized to receive inner penetrator or stylet 220 therein. Portions of inner penetrator 220 may be disposed within longitudinal passageway 184 extending through outer penetrator 210. The outside diameter of inner penetrator 220 and the inside diameter of longitudinal passageway 184 may be selected such that inner penetrator 220 may be slidably disposed within outer penetrator 210.

Metal disc 70 may be disposed within opening 186 for use in releasably attaching connector 180 with a magnetic drive shaft. For some applications, shaft 22 may be magnetized. End 223 of inner penetrator 220 is preferably spaced from metal disc 70 with insulating or electrically nonconductive material disposed therebetween.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment outer penetrator 210 and inner penetrator 220 may be ground together as one unit during an associated manufacturing process. Providing a matching fit allows respective tips 211 and 222 to act as a single drilling unit which facilitates insertion and minimizes damage as portions of penetrator assembly 160 are inserted into a bone and associated bone marrow. Inner penetrator 220 may also include a longitudinal groove (not expressly shown) that runs along the side of inner penetrator 220 to allow bone chips and/or tissues to exit an insertion site as penetrator assembly 160 is drilled deeper into an associated bone. Outer penetrator 210 may be formed from stainless steel, titanium or other materials of suitable strength and durability to penetrate bone.

Hub 200 may be used to stabilize penetrator assembly 160 during insertion of an associated penetrator into a patient's skin, soft tissue and adjacent bone at a selected insertion site. First end 201 of hub 200 may be operable for releasable engagement or attachment with associated connector 180. Second end 202 of hub 200 may have a size and configuration compatible with an associated insertion site for outer penetrator 210. The combination of hub 200 with outer penetrator 210 may sometimes be referred to as a "penetrator set" or intraosseous needle.

For some applications connector 180 may be described as a generally cylindrical tube defined in part by first end 181 and second end 182. The exterior of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. See FIG. 1A. Longitudinal ridges 190 also allow connector 180 to be grasped for disengagement from hub 200 when outer penetrator 210 has been inserted into a bone and associated bone marrow.

Second end 182 of connector 180 may include opening 185 sized to receive first end 201 of hub 200 therein. Threads 188 may be formed in opening 185 adjacent to second end 182 of connector 180. Threaded fitting 188 may be used in releasably attaching connector 180 with threaded fitting 208 adjacent to first end 201 of hub 200.

First end 201 of hub 200 may include a threaded connector 208 or other suitable fittings formed on the exterior thereof. First end 201 may have a generally cylindrical pin type configuration compatible with releasably engaging second end or box end 182 of connector 180.

For some applications end 202 of hub 200 may have the general configuration of a flange. Angular slot or groove 204 sized to receive one end of protective cover or needle cap 234 may be formed in end 202. Slot or groove 204 may be used to releasable engage cover 234 with penetrator assembly 160. See FIGS. 1A and 1C. For some applications cover 234 may be described as a generally hollow tube having rounded end 232. Cover 234 may be disposed within associated slot 204 to protect portions of outer penetrator 210 and inner penetrator 220 prior to attachment with an associated handle. Cover 234 may include a plurality of longitudinal ridges 236 formed on the exterior thereof. Longitudinal ridges 236 cooperate with each other to allow installing and removing cover or needle cap 234 without contaminating portions of an associated penetrator. Cover 234 may be formed from various plastics and/or metals.

The dimensions and configuration of second end 202 of hub 200 may be varied to accommodate various insertion sites and/or patients. Hub 200 may be satisfactorily used with a wide variety of flanges or other configurations compatible for contacting a patient's skin. Also, end 202 and associated flange may be used with a wide variety of hubs. The present invention is not limited to hub 200, end 202 or the associated flange. Passageway 206 may extend from first end 201 through second end 202. The inside diameter of passageway 206 may be selected to securely engage the outside diameter of penetrator 210. The dimensions and configuration of passageway 206 may be selected to maintain an associated penetrator assembly engaged with hub 200.

For some applications a penetrator assembly may include only a single, hollow penetrator. For other applications a penetrator assembly may include an outer penetrator such as a cannula, hollow needle or hollow drill bit and an inner penetrator such as a stylet, trocar or other removable device disposed within the outer penetrator. Penetrator 210 is one example of a single, hollow penetrator. See FIG. 1C. The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy. Some penetrators may be suitable for more than one purpose. The configuration and size of a penetrator may also vary depending upon the site chosen for insertion of each penetrator.

FIGS. 2A and 2B illustrate one mechanism for reloading apparatus 10a. As shown in FIG. 2A, spring 18 of apparatus 10a is in an uncompressed or fired position. Apparatus 10a may be placed against a hard surface, for example a table top, and apparatus 10a may be pushed against the hard surface to compress and reload or recock the spring. FIG. 2B shows apparatus 10a in a reloaded position with spring 18 compressed after pushing apparatus 10a against a hard surface.

FIGS. 3A and 3B illustrate an alternate embodiment of the invention in which apparatus 10b includes a ratchet mechanism engaged with spring-loaded assembly 16b. By way of example, ratchet lever 50 may be compressed by an operator in order to compress spring 18. Ratchet lever 50 is connected by pivot 52 to bar 54. Bar 54 is attached to first pawl 56. Second pawl 58 is attached to the inside surface of apparatus 10b. Sleeve 60 extends over first end of rod 20 and includes teeth 62 configured to engage with pawls 56 and 58. Sleeve 60 includes sleeve plate 66 which compresses spring 18 as sleeve 60 is moved in a forward direction by the ratchet mechanism. When ratchet lever 50 is compressed by an operator, first pawl 56, engages with teeth 62 of sleeve 60 and moves sleeve 20 in a forward direction causing sleeve plate 66 to compress spring 18. As first pawl 56 moves along sleeve 60, second pawl 58 holds sleeve 60 in a further advanced position. Spring 18 is thereby compressed in a back-to-front direction.

FIG. 3B illustrates spring-loaded mechanism in a loaded position with spring 18 compressed and ready to fire. When spring 18 is in a compressed position rod 20 extends beyond first end of sleeve 60. The ratchet mechanism functions to compress spring 18, thereby reloading apparatus 10b and also enables the adjustment of spring-loaded assembly 16b to a desired level of tension such that the firing power and firing depth of apparatus 10b may be adjusted.

FIG. 3C illustrates a ratchet mechanism that functions by compressing spring 18 of apparatus 10c in a front-to-back direction. Ratchet lever 70 is connected to elongated pawl 74 by pin 72. Ratchet lever 70 pivots at point 76. Second pawl 78 is attached to inner surface of apparatus 10c. First end of rod 80 includes teeth 82. When ratchet lever 70 is compressed by an operator, elongated pawl 74 engages teeth 82 of rod 80 and moves rod 80 in a front-to-back direction, thus compressing spring 18 in a front-to-back direction. Second pawl 78 functions to maintain the compressed position of rod 80 after first pawl 76 has moved it in a front to back direction. This motion causes the ratchet mechanism to further compress spring 18. The ratchet mechanism also enables the adjustment of spring-loaded assembly 16c. Other ratchet mechanisms may be employed to compress spring 18 of apparatus 10b and 10c which may or may not include pawls, pivots or rod extensions.

Figure 4:
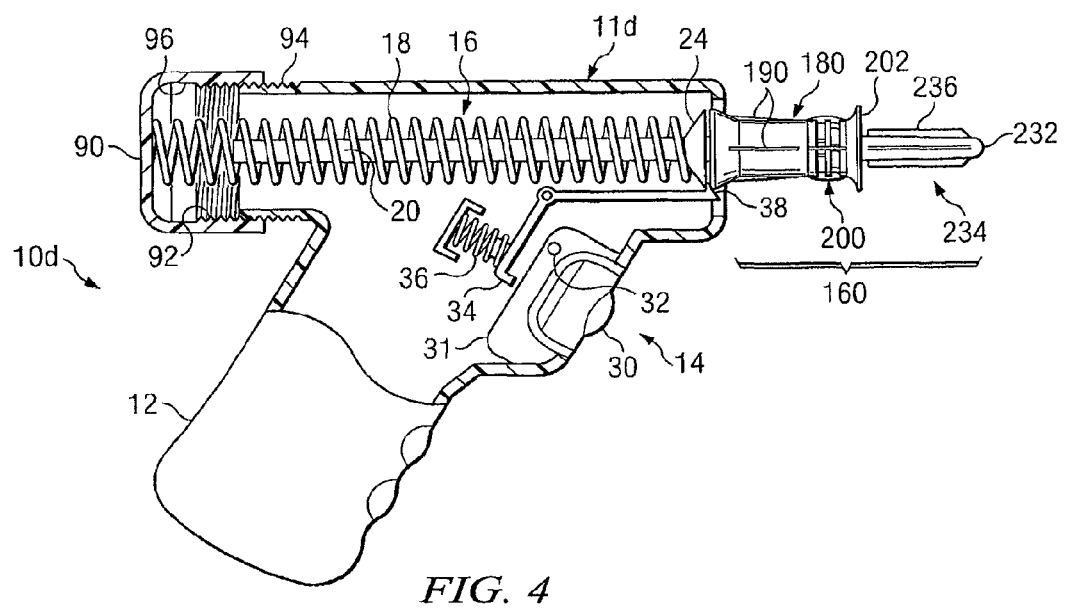
FIG. 4 shows an example illustration of an apparatus operable for penetrating the bone marrow of a bone.

FIG. 4 illustrates one embodiment of a mechanism for adjusting the tension or propelling force of spring 18. By way of example, apparatus 10d includes spring adjustment cap 90. Cap 90 includes inner threads 92 which extend circumferentially along inner surface 96 of cap 90. Inner threads 92 are configured to engage outer threads 94 of housing 11d of apparatus 10d when an operator advances cap 90 with a twisting or turning motion. Advancing cap 90 decreases the space within which spring-loaded assembly 16 is situated and thereby compresses spring 18. This motion adjusts the degree of compression of spring 18 and the ensuing power with which it propels penetrator assembly 160. For smaller softer bones, adjusting cap 90 is unscrewed to lengthen the compressed spring. For increasing the force for larger stronger bones, cap 90 is advanced by rotating it on a threaded housing to shorten spring 18, thus increasing the compression and stored kinetic energy. This embodiment allows a single-sized apparatus to be applied to a wide spectrum of bone sizes and shapes including adult bones, bones of children, and bones of animals. It permits the device to be applied to thicker bones like the tibia and humeral head as well as to thinner bones like the sternum.

In one embodiment of the invention steps for penetrating into bone marrow may include firing apparatus 10a, 10b, 10c or 10d (See FIGS. 1A-4) to insert penetrator assembly 160 into a bone and associated bone marrow, disengaging an associated shaft from connector 180 and disengaging connector 180 from associated hub 200 leaving hub 200 and attached penetrator 210 disposed in the bone marrow. The depth of penetration into a bone and associated bone marrow may be determined by the degree of tension in compressed spring 18. For some applications, threaded connection or fitting 208 may allow attachment with various types of Luer locks and/or Luer fittings associated with of intravenous tubing or a syringe with first end 201 of hub 200.

Apparatus and methods incorporating teachings of the present invention may be used with a wide variety of handles, connectors, hubs and penetrators. The present invention is not limited to handles, connectors, flanges, penetrators and/or penetrator assemblies as shown in FIGS. 1A-4. For some applications a handle or driver may be directly attached to a penetrator hub without the use of a connector.

Although the present invention and its advantages have been described in detail, it should be understood that various changes, substitutions and alterations can be made herein without departing from the spirit and scope of the invention as defined by the following claims.

What is claimed is:

1. An apparatus for penetrating a bone marrow of a bone comprising:
    a pistol-shaped housing including a body portion, a handle, and a trigger mechanism, the handle oriented at a fixed, non-parallel angle relative to the body portion and configured to be gripped by a user's hand;
    a spring-loaded assembly disposed in the housing at an angle with respect the handle, the spring-loaded assembly including a spring surrounding a rod having a first end and a second end and a shaft extending from the second end of the rod;
    an adjustment mechanism associated with the spring-loaded assembly at the first end of the rod, the adjustment mechanism operable to adjust a tension of the spring in the spring-loaded assembly; and
    a penetrator assembly operable to be releasably engaged with the shaft, the penetrator assembly including a penetrator extending therefrom operable to penetrate the bone and access the bone marrow.

2. The apparatus of claim 1, wherein the penetrator assembly comprises:
    a connector including a first end and a second end, the first end of the connector operable to releasably engage the shaft; and
    a hub including a first end and a second end, the first end of the hub operable to releasably engage the second end of the connector and the penetrator extending from the second end of the hub.

3. The apparatus of claim 2, wherein the second end of the connector and the first end of the hub include threaded connections operable to provide releasable engagement of the connector and the hub.

4. The apparatus of claim 2, wherein the second end of the hub includes a flange sized to be compatible with a selected insertion site for the penetrator.

5. The apparatus of claim 1, further comprising a magnetic disc disposed in the penetrator assembly operable to provide releasable engagement with the shaft.

6. The apparatus of claim 1, wherein the penetrator includes a hollow outer penetrator and a tip having at least one cutting surface.

7. The apparatus of claim 6, wherein the penetrator further includes a trocar sized to be received by the hollow outer penetrator.

8. The apparatus of claim 1, wherein the adjustment mechanism comprises:
    a cap including a first thread extending circumferentially along an inner surface; and a second thread extending circumferentially along an outer surface of the housing proximate the first end of the rod, the second thread of the housing operable to engage the first thread of the cap in order to adjust the tension of the spring in the spring-loaded assembly.

9. The apparatus of claim 1, further comprising:
    a protrusion disposed on the second end of the rod, the protrusion operable to position the spring on the rod; and
    an L-shaped bar coupled to the trigger mechanism, the L-shaped bar including a projection operable to engage the protrusion on the second end of the rod in order to hold the spring in a compressed position.

10. The apparatus of claim 1, wherein the trigger mechanism includes a button operable to be compressed by a finger of an operator to activate the spring-loaded assembly and propel the penetrator into the bone and the bone marrow.

11. The apparatus of claim 1, wherein the spring is selected from a group consisting of a coiled spring, a leaf spring and a bellows.

12. A method of accessing bone marrow of a bone comprising:
   applying an apparatus comprising:
      a housing comprising a body portion, a handle, and a trigger mechanism, the handle oriented at a fixed, non-parallel angle relative to the body portion and configured to be gripped by a user's hand;
      a spring-loaded assembly disposed in the housing, the spring-loaded assembly including a spring surrounding a rod having a first end and a second end and a shaft extending from the second end of the rod;
      an adjustment mechanism associated with the spring-loaded assembly at the first end of the rod; and
      a penetrator assembly operable to be releasably engaged with the shaft, the penetrator assembly including a penetrator extending therefrom operable to penetrate the bone and access the bone marrow;
   adjusting a tension of the spring using the adjustment mechanism of the apparatus based on a type of bone to be accessed; and
   activating the trigger mechanism of the apparatus to insert the penetrator into the bone and access the bone marrow.

13. The method of claim 12, wherein adjusting the tension of the spring using the adjustment mechanism of the apparatus comprises adjusting a degree of compression of the spring and a power that penetrator is inserted into the bone.

14. The method of claim 12, wherein the adjustment mechanism comprises:
   a cap including a first thread extending circumferentially along an inner surface; and
   a second thread extending circumferentially along an outer surface of the housing proximate the first end of the rod, the second thread of the housing operable to engage the first thread of the cap in order to adjust the tension of the spring in the spring-loaded assembly.

15. The method of claim 14, wherein adjusting the tension of the spring using the adjustment mechanism of the apparatus comprises:
   unscrewing the cap toward the first end of the rod to lengthen the spring for small bones; and
   screwing the cap toward the second end of the rod to shorten the spring for large bones.

16. The method of claim 12, wherein the penetrator assembly comprises:
   a connector including a first end and a second end, the first end of the connector operable to releasably engage the shaft; and
   a hub including a first end and a second end, the first end of the hub operable to releasably engage the second end of the connector and the penetrator extending from the second end of the hub.

17. The method of claim 16, further comprising detaching the apparatus from the connector.

18. The method of claim 17, further comprising detaching the connector from the penetrator hub while the penetrator remains disposed in the bone and the bone marrow.

19. The method of claim 12, wherein the apparatus further comprising:
   a protrusion disposed on the second end of the rod, the protrusion operable to position the spring on the rod; and
   an L-shaped bar coupled to the trigger mechanism, the L-shaped bar including a projection operable to engage the protrusion on the second end of the rod in order to hold the spring in a compressed position.

20. The method of claim 19, wherein activating the trigger mechanism of the apparatus comprising compressing a button on the trigger mechanism to disengage the projection on the L-shaped bar from the protrusion on the second end of the rod and activate the spring loaded assembly to propel the penetrator into the bone and the bone marrow.

* * * * *